United States Patent
Fujii et al.

(10) Patent No.: US 7,977,586 B2
(45) Date of Patent: Jul. 12, 2011

(54) WEIGHT SENSOR AND BALANCE CONTROLLER FOR A BLOOD PURIFICATION SYSTEM

(75) Inventors: Junya Fujii, Hiroshima (JP); Shogo Kamito, Hiroshima (JP); Toshiyuki Endo, Gifu (JP); Youichi Sansho, Saitama (JP)

(73) Assignee: JMS Co., Ltd., Hiroshima (JP)

( * ) Notice: Subject to any disclaimer, the term of this patent is extended or adjusted under 35 U.S.C. 154(b) by 278 days.

(21) Appl. No.: 12/296,535

(22) PCT Filed: Apr. 12, 2007

(86) PCT No.: PCT/JP2007/058075
§ 371 (c)(1),
(2), (4) Date: Oct. 9, 2008

(87) PCT Pub. No.: WO2007/119786
PCT Pub. Date: Oct. 25, 2007

(65) Prior Publication Data
US 2009/0276099 A1 Nov. 5, 2009

(30) Foreign Application Priority Data
Apr. 14, 2006 (JP) .................. 2006-112621

(51) Int. Cl.
G01G 17/04 (2006.01)
G01G 21/16 (2006.01)
G01G 3/14 (2006.01)
A61M 1/14 (2006.01)
A61M 1/34 (2006.01)

(52) U.S. Cl. ..... 177/45; 604/65; 604/500; 128/DIG. 13; 177/199; 177/245

(58) Field of Classification Search .................... 177/45, 177/50, 229, 245, 199, 200; 604/65, 318, 604/500; 128/DIG. 13
See application file for complete search history.

(56) References Cited

U.S. PATENT DOCUMENTS

| 3,135,112 | A | * | 6/1964 | Farley | 73/862.382 |
| 3,602,866 | A | * | 8/1971 | Saxl | 177/211 |
| 4,558,756 | A | * | 12/1985 | Seed | 177/211 |
| 4,650,464 | A | * | 3/1987 | Ruiz et al. | 604/500 |
| 4,678,049 | A | * | 7/1987 | Gummere et al. | 177/229 |

(Continued)

FOREIGN PATENT DOCUMENTS
DE 19857381 A1 7/2000
(Continued)

OTHER PUBLICATIONS

English language Abstract of JP 64-066520 A, Mar. 13, 1989.

(Continued)

*Primary Examiner* — Randy W Gibson
(74) *Attorney, Agent, or Firm* — Greenblum & Bernstein, P.L.C.

(57) ABSTRACT

A weight sensor includes an arm having an end fixed to a pillar and a free end; a filtrate holder, a replacement fluid holder, and a dialysate holder provided at three locations of the arm along a longitudinal direction of the arm to hold respective substances; a first strain value sensor, a second strain value sensor, and a third strain value sensor each of which detects a strain value of the arm corresponding to a total weight of the substances held by the holders ranging from a holder proximate to the free end to a corresponding holder; and a weight calculation unit that calculates the total and each of the weights from the obtained detection results.

16 Claims, 10 Drawing Sheets

U.S. PATENT DOCUMENTS

| | | | |
|---|---|---|---|
| 4,712,567 A * | 12/1987 | Gille et al. | 600/584 |
| 6,590,167 B2 * | 7/2003 | Clare | 600/584 |
| 7,076,990 B2 * | 7/2006 | Yoshikuwa | 73/1.13 |

FOREIGN PATENT DOCUMENTS

| | | | |
|---|---|---|---|
| EP | 2019296 A1 * | 1/2009 | |
| GB | 2182156 A | 5/1987 | |
| JP | 6-90067 B2 | 11/1994 | |
| JP | 9-239024 A | 9/1997 | |
| JP | 2003-214938 A | 7/2003 | |
| JP | 2006-105734 A | 4/2006 | |

OTHER PUBLICATIONS

English language Abstract of JP 2003-214938 A, Jul. 30, 2003.
English language Abstract of JP 9-239024 A, Sep. 16, 1997.
English language Abstract of JP 2006-105734 A, Apr. 20, 2006.
U.S. Appl. No. 12/278,427 to Fujii et al., filed Aug. 6, 2008.

* cited by examiner

| Weight of filtrate in filtrate container | Weight of discarded filtrate | Flow rate of filtrate |
|---|---|---|
| 300g(0~700g) | 5.20kg(0~150.00kg) | 2000ml/h(0~6000ml/h) |

| Weight of replacement fluid in replacement fluid container | Weight of used replacement fluid | Flow rate of replacement fluid |
|---|---|---|
| 100g(500~0g) | 2.00kg(0~50.00kg) | 1000ml/h(0~3000ml/h) |

| Weight of dialysate in dialysate container | Weight of used dialysate | Flow rate of dialysate |
|---|---|---|
| 100g(500~0g) | 3.00kg(0~50.00kg) | 1000ml/h(0~3000ml/h) |

WEIGHT SENSOR AND BALANCE CONTROLLER FOR A BLOOD PURIFICATION SYSTEM

TECHNICAL FIELD

The present invention relates to a weight sensor that detects a weight of a substance, and a balance controller that balances among weights of plural substances.

BACKGROUND ART

Conventionally, in order to purify blood of patients with renal function insufficiency, for example, medical treatments using Continuous Hemofiltration (CHF), Continuous Hemodiafiltration (CHDF), and/or the like have been performed. In the CHF, blood taken from a patient is provided to a blood purifier having a semipermeable membrane (hemofiltration membrance) for hemofiltration, and then filtered by the hemofiltration membrane to generate purified blood. The purified blood is returned to the patient body, and waste products (electrolytic substance such as urea and sodium chloride, for example) and solvent (water) resulting from the hemofiltration are discarded. In parallel, a predetermined replacement fluid is supplied to blood of the patient so as to supplement a decrease in solvent of the blood. The above processing is performed continually and slowly. In the CHF, waste products and solvent which are taken from blood in order to be discarded are called filtrate.

On the other hand, the CHDF is a method of improving a capability of removing small molecules in the CHF. In the CHDF, dialysis as well as the CHF are performed. More specifically, in the CHDF, a blood purifier having a dialysis membrane in addition to a hemofiltration membrane is used. The blood purifier is provided also with dialysate. Waste products still included in the purified blood after hemofiltration are sent to the dialysate through the dialysis membrane, so that the waste products can be removed from the blood. Then, the blood purified by the hemofiltration and the dialysis is returned to the patient body and a replacement fluid is supplied to the blood of the patient. The above processing is performed continuously and slowly. In the CHDF, waste product and solvent which are taken from the blood during hemofiltration, and used dialysate are called filtrate.

In the meanwhile, a sudden change in an amount of blood in a patient body causes rapid deterioration of patient's condition. In order to avoid such situations, it is necessary to keep a balance between (i) a flow rate of blood taken from the patient and (ii) a total flow rate of blood returned to the patient and replacement fluid supplied to the patient. The following explains blood purification systems using the CHDF that keep a balance between (i) a flow rate of blood taken from a patient and (ii) a total flow rate of blood returned to the patient and replacement fluid supplied to the patient. There are a first scheme, a second scheme (disclosed in Patent Reference 1, for example), and a third scheme as blood purification systems. The first scheme, the second scheme, and the third scheme of blood purification systems are sequentially explained below.

Firstly, the first scheme of blood purification system is explained with reference to FIG. 1. FIG. 1 is a block diagram of the first scheme of blood purification system which keeps, within a predetermined range, a difference between (i) a total weight of dialysate and replacement fluid and (ii) a weight of filtrate. In the first scheme of blood purification system as shown in FIG. 1, a blood pump 6 sends blood taken from a patient A to a blood purifier 10 via an artery-side blood circuit 11. The blood purifier 10 has a hemofiltration membrane to remove water from the taken blood. A dialysate pump 7 sends dialysate contained in a dialysate container 3 to the blood purifier 10 via a dialysate supply channel 12. The blood purifier 10 removes water and waste products from the taken blood via the filtrate (dialysis) membrane. The blood purified by the blood purifier 10 is returned to the patient A via a vein-side blood circuit 13. A replacement fluid pump 8 mixes a replacement fluid contained in a replacement fluid container 4 into the vein-side blood circuit 13, thereby supplying the replacement fluid together with the purified blood into the patient A. A filtrate pump 9 sends, as filtrate, the used dialysate and the waste products which are taken from the blood by the blood purifier 10, from the blood purifier 10 to a filtrate container 5 via a filtrate discard channel 14. A dialysate/replacement fluid weight measuring device 91 measures a total weight of dialysate contained in the dialysate container 3 and replacement fluid contained in the replacement fluid container 4. A filtrate weight measuring device 92 measures a weight of filtrate contained in the filtrate container 5. A control unit 93 controls operations, such as the number of rotations, of the dialysate pump 7, the replacement fluid pump 8, and the filtrate pump 9, in order to keep, within a predetermined range, a difference between (i) the total weight of the dialysate and the replacement fluid measured by the dialysate/replacement fluid weight measuring device 91 and (ii) the weight of the filtrate measured by the filtrate weight measuring device 92. This achieves a balance between (i) a flow rate of blood taken from a patient and (ii) a total flow rate of blood returned to the patient and replacement fluid supplied to the patient.

Secondly, the second scheme of blood purification system is explained with reference to FIG. 2. FIG. 2 is a block diagram of the second scheme of blood purification system which calculates a flow rate of to-be-used dialysate, a flow rate of to-be-used replacement fluid, and a flow rate of to-be-discarded filtrate, using respective different weight measuring devices, and thereby keeps the flow rates to have predetermined values, respectively. The second scheme of blood purification system of FIG. 2 differs from the first scheme of blood purification system of FIG. 1 in the following. That is, in the second scheme of blood purification system, to-be-used dialysate is acquired and stored into a dialysate acquisition container 101, and an acquired-dialysate weight measuring device 102 measures a weight of the dialysate contained in the dialysate acquisition container 101. A control unit 107 calculates an amount of a temporal change (hereinafter, referred to also as a "temporal change amount") in the weight of the dialysate measured by the acquired-dialysate weight measuring device 102, and thereby calculates a flow rate of currently-using dialysate. Then, the control unit 107 controls operations, such as the number of rotations, of a dialysate pump 7 to keep the calculated flow rate of the dialysate to be a predetermined flow rate. Likewise, to-be-used replacement fluid is acquired and stored into a replacement fluid acquisition container 103, and an acquired-replacement-fluid weight measuring device 104 measures a weight of the replacement fluid contained in the replacement fluid acquisition container 103. The control unit 107 calculates a temporal change amount of the weight of the replacement fluid measured by the acquired-replacement-fluid weight measuring device 104, and thereby calculates a flow rate of currently-using replacement fluid. Then, the control unit 107 controls operations, such as the number of rotations, of a replacement fluid pump 8 to keep the calculated flow rate of the replacement fluid to be a predetermined flow rate. Filtrate to be discarded is acquired and stored into a filtrate acquisition container 105, and an acquired-filtrate weight measuring device 106 measures a weight of the filtrate contained in the filtrate acquisition container 105. The control unit 107 calculates a temporal change amount of the weight of the filtrate measured by the acquired-filtrate weight measuring device 106, and thereby calculates a flow rate of currently discarding filtrate. Then, the control unit 107 controls operations, such as the number of rotations, of a filtrate pump 9 to keep the calculated flow rate of the filtrate to be a predetermined flow rate. This achieves a balance between (i) a flow rate of blood taken from a patient and (ii) a total flow rate of blood returned to the patient and replacement fluid supplied to the patient.

Finally, the third scheme of blood purification system is explained. As described above, the second scheme of blood purification system separately calculates a flow rate of to-be-used dialysate, a flow rate of to-be-used replacement fluid, and a flow rate of to-be-discarded filtrate, using respective different weight measuring devices, and thereby keeps the flow rates to have predetermined values, respectively. On the other hand, the third scheme of blood purification system calculates a flow rate of to-be-used dialysate, a flow rate of to-be-used replacement fluid, and a flow rate of to-be-discarded filtrate, using a single weight measuring device that is used by being sequentially delayed to measure respective liquids. As a result, flow rates of the respective liquids are kept to be predetermined values, respectively. This achieves a balance between (i) a flow rate of blood taken from a patient and (ii) a total flow rate of blood returned to the patient and replacement fluid supplied to the patient.

Patent Reference 1: Japanese Unexamined Patent Application Publication No. 9-239024

DISCLOSURE OF INVENTION

Problems that Invention is to Solve

However, the above-explained three schemes of blood purification system have their problems.

As explained above, the first scheme of blood purification system keeps, within a predetermined range, a difference between (i) a total weight of dialysate and replacement fluid and (ii) a weight of filtrate, thereby achieving a balance between (i) a flow rate of blood taken from a patient and (ii) a total flow rate of blood returned to the patient and replacement fluid supplied to the patient. However, it is impossible to completely and accurately measure weights and flow rates of to-be-used dialysate and to-be-used replacement fluid. Thereby, in the case of medical treatments using the CHDF, when dialysate or replacement fluid is to be supplied in the middle of the treatment, it is not sure how much of the liquid should be supplied. It is not clear either how much of the liquid should be prepared for a next treatment. As a result, large excess amounts of dialysate and replacement fluid should be prepared in order not to be run out during medical treatments.

The second and third schemes of blood purification system calculate a total flow rate of to-be-used dialysate and to-be-used replacement fluid, and also a flow rate of to-be-discarded filtrate, as described above. However, there is an error between each calculated flow rate and an actual flow rate. Therefore, even if the calculated flow rate of each liquid is kept to have a corresponding predetermined value, there is a high possibility of failing to control for balancing between (i) a flow rate of blood taken from a patient and (ii) a total flow rate of blood returned to the patient and replacement fluid supplied to the patient. The failure in balance results in deterioration of patient's condition.

As explained above, the conventional devices and methods cannot simultaneously achieve both of (i) balance among weights of plural substances and (ii) detection of the respective weights of the substances.

Thus, the present invention overcomes the conventional problems. It is an object of the present invention to provide a weight sensor that detects respective correct weights of plural substances, and a balance controller that achieves a balance among the weights of the substances with a high accuracy.

Means to Solve the Problems

In accordance with an aspect of the present invention for achieving the object, there is provided a weight sensor including: a pillar; an arm having an end fixed to the pillar and a free end; n holders, provided at n locations on a side surface of the arm arranged along a longitudinal direction, respectively, each of which is configured to hold a substance, n being a natural number equal to or greater than two; n strain value sensors, provided on the arm in association with n sums, respectively, each of which is configured to detect a strain value of the arm corresponding to a corresponding sum among the n sums, the corresponding sum being a sum of weights of the substances held by the holders ranging from a holder proximate to the free end to a m-th holder counted from the pillar, and m being a natural number ranging from 1 to n; and a weight calculation unit configured to calculate the n sums based on results of the detection of the n strain value sensors.

For example, when a part of substance held by the second holder counted from the pillar is transferred to a holder proximate to the pillar via a predetermined part, the transfer does not affect a total weight (sum of weights) of substances held by holders ranging from the holder proximate to the pillar to a holder proximate to the free end of the arm. What the weight sensor according to the present invention calculates is the total weight (sum of weights). Therefore, by monitoring the total weight (sum of weights) calculated by the weight sensor according to the present invention, it is possible to balance between (i) an amount of decrease in the substance held by the second holder counted from the pillar and (ii) an amount of increase or decrease in the substance held by the holder proximate to the pillar. That is, the weight sensor according to the present invention is used to balance among weights of a plurality of substances.

As another example, if the number of the holders is two, the weight sensor according to the present invention detects a weight of the substance held by the holder proximate to the free end of the arm, and also detects a sum of weights of substances held by the two holders. The sum is subtracted by the weight of the substance held by the holder proximate to the free end of the arm, thereby calculating a weight of the substance held by the holder proximate to the pillar. That is, the weight sensor according to the present invention is used to calculate a weight of each of the plurality of substances.

The weight calculation unit may be configured to calculate the weights of the substances held by the n holders, respectively, based on results of the detection of the n strain value sensors.

The weight sensor may further include a display unit configured to display results of the calculation of the weight calculation unit.

The arm may be a member including n bar-shaped members connected in series at each end, each of the n bar-shaped members may have a hole penetrating in a direction perpendicular to the longitudinal direction of the arm without penetrating the side surface, and the n holders may be provided on the n bar-shaped members, respectively.

A shape of the hole in a cross section may be symmetry with respect to a bisector of a line segment perpendicular to the longitudinal direction of the arm in the cross section of the hole, and also symmetry with respect to a bisector of a line segment along the longitudinal direction of the arm in the cross section of the hole.

A size of each of a closer end and a farther end of the cross section of the hole may be larger than a size of a part of the cross section of the hole between the closer end and the farther end, the closer end being closer to the pillar and an farther end being farther from the pillar.

The n strain value sensors may be Roberval strain value sensors provided on the n bar-shaped members, respectively.

The arm may have holes each of which penetrates in a direction perpendicular to the longitudinal direction of the arm without penetrating the side surface, the holes being provided between the pillar and the holder proximate to the pillar and between two neighboring holders, respectively.

A shape of each of the holes in a cross section may be symmetry with respect to a bisector of a line segment perpendicular to the longitudinal direction of the arm in the cross section of the hole, and also symmetry with respect to a bisector of a line segment along the longitudinal direction of the arm in the cross section of the hole.

A size of each of a closer end and a farther end of the cross section of the hole may be larger than a size of a part of the cross section of the hole between the closer end and the farther end, the closer end being closer to the pillar and an farther end being farther from the pillar.

The n strain value sensors may be Roberval strain value sensors, and the n strain value sensors are provided between the pillar and the holder proximate to the pillar and between the two neighbor holders, respectively and separately.

The weight sensor may further include an increased/decreased amount calculation unit configured to calculate an amount of increase or decrease in a weight of the substance held by each of the n holders from an initial weight of the substance, based on results of the calculation of the n weight calculation units.

The weight sensor may further include a temporal change amount calculation unit configured to calculate an amount of a temporal change in a weight of the substance held by each of the n holders, based on results of the calculation of the n weight calculation units.

In accordance with another aspect of the present invention, there is provided a balance controller including: an obtainment unit configured to obtain a sum of weights of substances calculated by the weight sensor according to the above aspect, the substances being held by the holders that are from a holder proximate to the free end of the arm to a holder proximate to the pillar; and a control unit configured to control temporal change amounts of the weights of the substances held by the holders, respectively, in order to keep the sum obtained by the obtainment unit within a predetermined range.

The number of the holders may be three, a first holder in the holders may hold filtrate, a second holder in the holders may hold replacement fluid, and a third holder in the holders may hold dialysate, and the control unit may be configured to keep a sum of a weight of the filtrate, a weight of the replacement fluid, and a weight of the dialysate within a predetermined range, so as to balance between an amount of temporal increase in the filtrate and an amount of temporal decrease in the replacement fluid and the dialysate.

The number of the n holders may be two, a first holder in the holders may hold filtrate, and a second holder in the holders may hold replacement fluid, and the control unit may be configured to keep a sum of a weigh of the filtrate and a weight of the replacement fluid within a predetermined range, so as to balance between an amount of temporal increase in the filtrate and an amount of temporal decrease in the replacement fluid.

Effects of the Invention

Thus, the present invention can provide a weight sensor that detects respective weights of plural substances, and a balance controller that achieves a balance among the weights of the plural substances.

BRIEF DESCRIPTION OF DRAWINGS

FIG. 6 is a diagram showing one example of a screen on which a display 33 of the weight sensor 1 displays calculation results, according to first embodiment.

Figure 1:
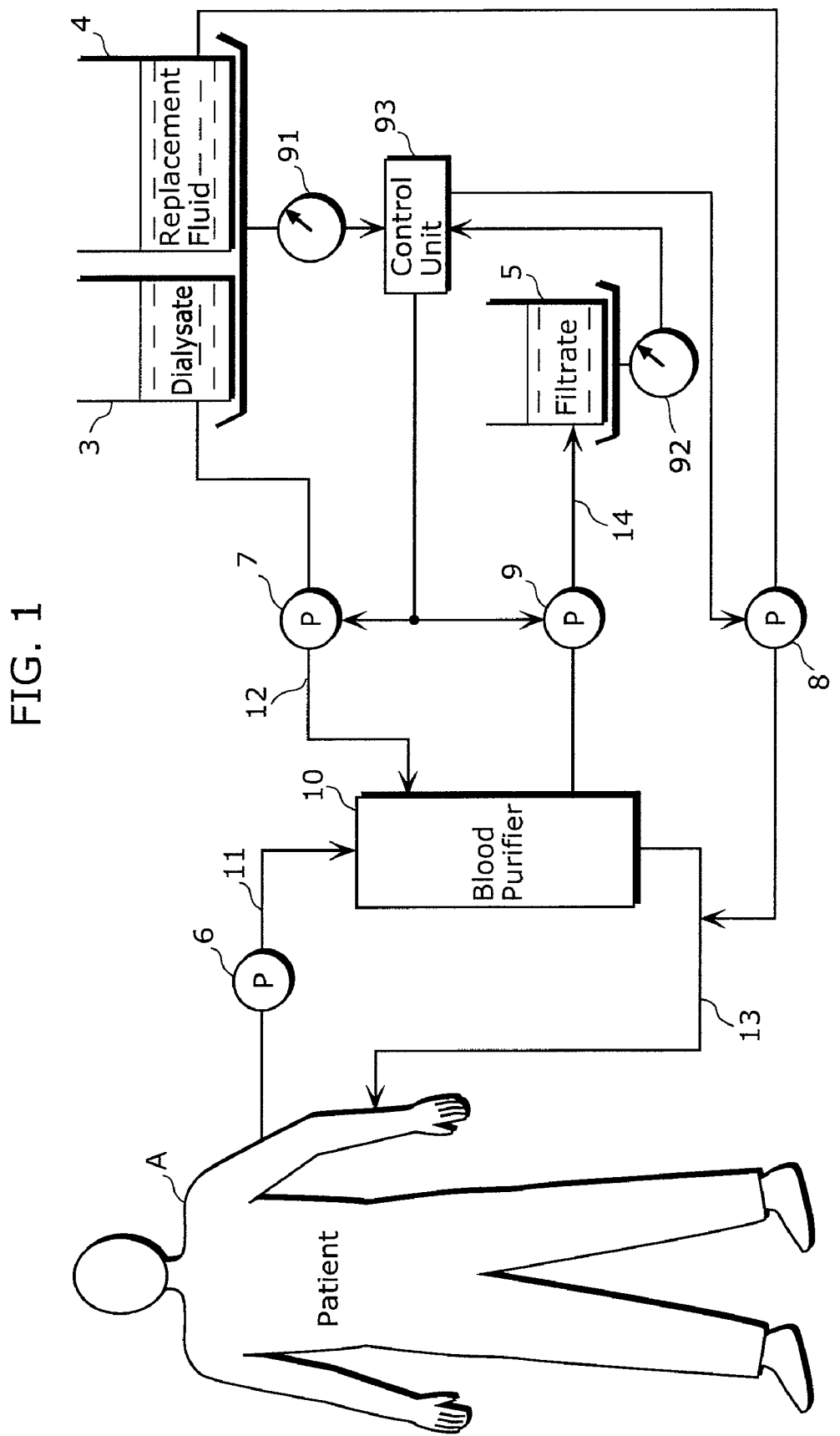
FIG. 1 is a block diagram of a conventional blood purification system.
Figure 2:
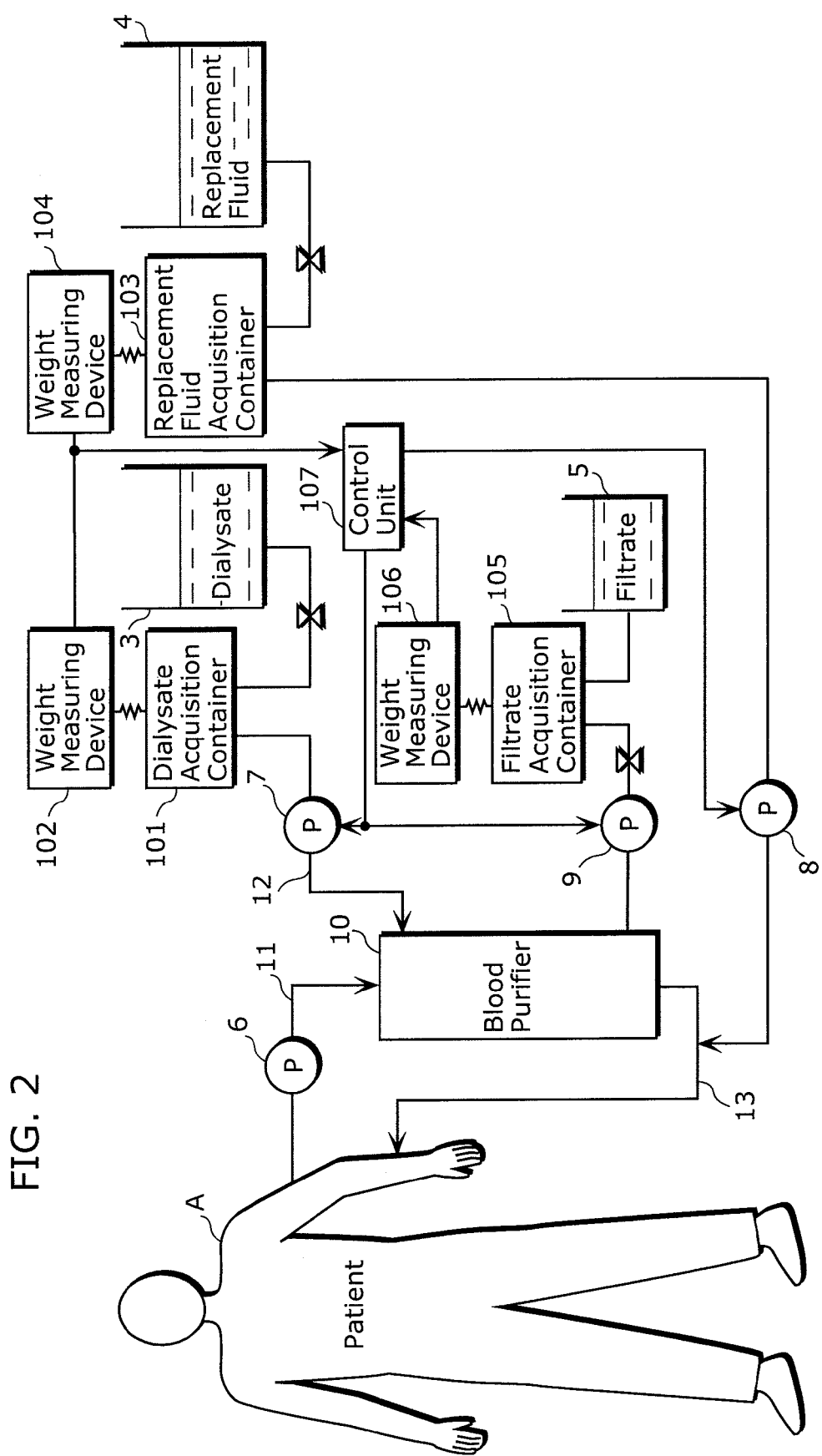
FIG. 2 is a block diagram of another conventional blood purification system.

NUMERICAL REFERENCES 1 weight sensor
2 balance controller
3 dialysate container
4 replacement fluid container
5 filtrate container
6 blood pump
7 dialysate pump
8 replacement fluid pump
9 filtrate pump
10 blood purifier
11 artery-side blood circuit
12 dialysate supply channel
13 vein-side blood circuit
14 filtrate discard channel
21 base
22 pillar
23 arm
23$a$ first square bar
23$b$ second square bar
23$c$ third square bar
24 filtrate holder
25 replacement fluid holder 26 dialysate holder
27 first strain value sensor
28 second strain value sensor
29 third strain value sensor
30 weight calculation unit
31 increased/decreased amount calculation unit
32 temporal change amount calculation unit
33 display unit
41 obtainment unit
42 control unit

BEST MODE FOR CARRYING OUT THE INVENTION

The following describes preferred embodiments according to the present invention with reference to the drawings.

First Embodiment

Firstly, a structure of a blood purification system according to the first embodiment is described with reference to FIGS. 3 to 6.

Figure 3:
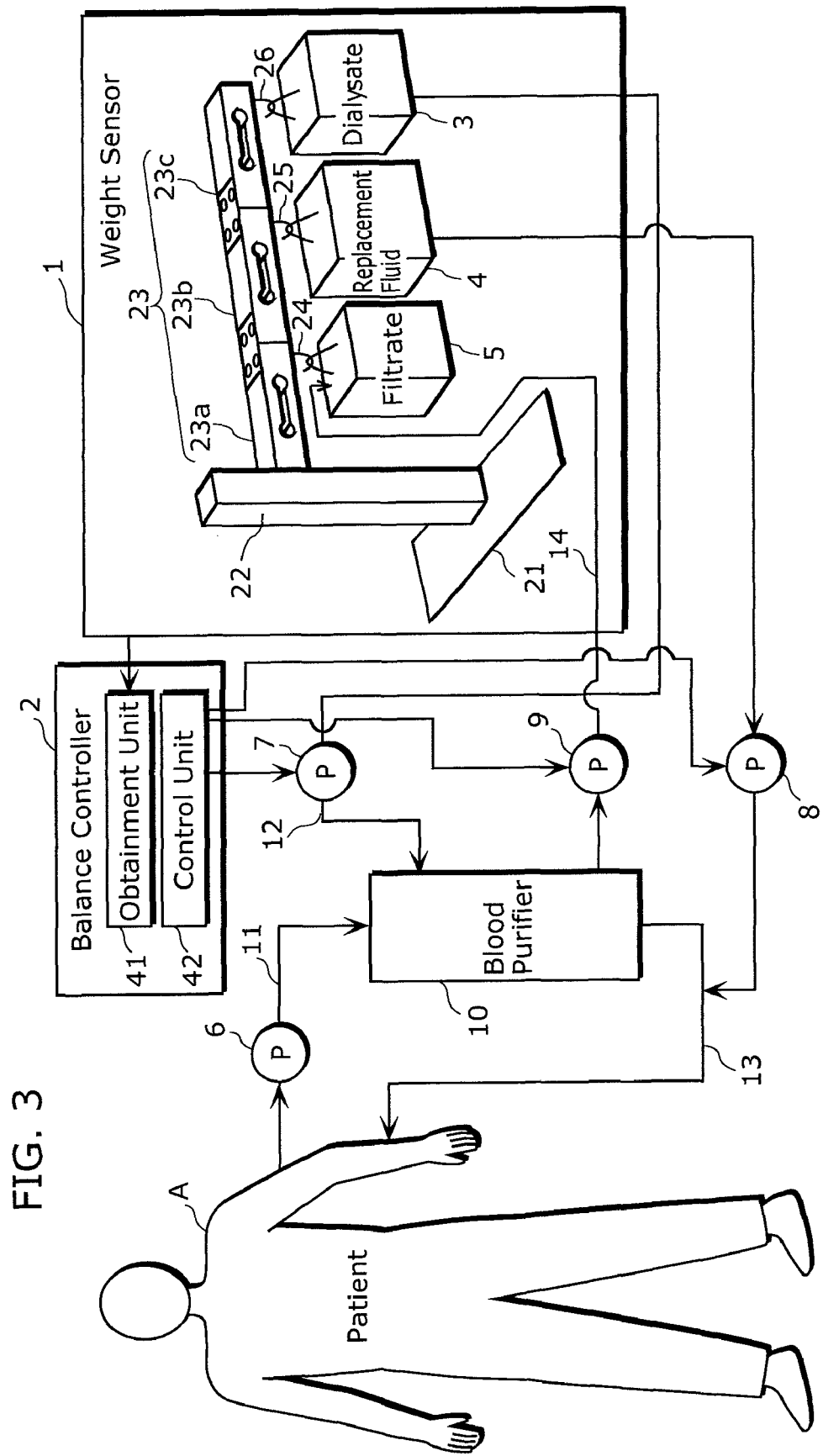
FIG. 3 is a block diagram of a blood purification system according to a first embodiment of the present invention.

FIG. 3 is a block diagram of the blood purification system according to the first embodiment. The blood purification system according to the first embodiment is used, for example, when a medical treatment using the CHDF is applied to a patient A having a renal function insufficiency to purify his/her blood. This blood purification system balances between (i) a total flow rate of dialysate and replacement fluid that are currently used in the treatment and (ii) a flow rate of filtrate that is currently discarded, and also calculates and displays an amount of temporal change (namely, a flow rate) in each of the dialysate, the replacement fluid, and the filtrate. As shown in FIG. 3, the blood purification system according to the first embodiment includes a weight sensor 1, a balance controller 2, a dialysate container 3, a replacement fluid container 4, a filtrate container 5, a blood pump 6, a dialysate pump 7, a replacement fluid pump 8, a filtrate pump 9, a blood purifier 10, an artery-side blood circuit 11, a dialysate supply channel 12, a vein-side blood circuit 13, and a filtrate discard channel 14.

The weight sensor 1 is used to balance between (i) a total flow rate of using dialysate and using replacement fluid and (ii) a flow rate of discarding filtrate. The weight sensor 1 detects a weight, a flow rate that is a temporal change amount of the weight, and the like regarding each of dialysate, replacement fluid, and filtrate. Then, the weight sensor 1 displays the detected results. More detailed structure of the weight sensor 1 is described later with reference to FIG. 4. Based on the results detected by the weight sensor 1, the balance controller 2 controls operations of the dialysate pump 7, the replacement fluid pump 8, and the filtrate pump 9 to balance between (i) a total flow rate of using dialysate and using replacement fluid and (ii) a flow rate of discarding filtrate. The balance controller 2 includes: an obtainment unit 41 that obtains the results detected by the weight sensor 1; and a control unit 42 that controls operations of the dialysate pump 7, the replacement fluid pump 8, and the filtrate pump 9.

The dialysate container 3 is a container in which dialysate to be used is contained. The replacement fluid container 4 is a container in which replacement fluid to be used is contained. The filtrate container 5 is a container in which filtrate to be discarded is contained. Each of the dialysate container 3, the replacement fluid container 4, and the filtrate container 5 has a handle on the top of the container. Using the above-mentioned handle, the dialysate container 3 is held by a dialysate holder 26 in the weight sensor 1. Likewise, using respective handles, the replacement fluid container 4 and the filtrate container 5 are held by a replacement fluid holder 25 and a filtrate holder 24 in the weight sensor 1, respectively.

The blood pump 6 sends blood taken from the patient A to the blood purifier 10. The dialysate pump 7 sends the dialysate contained in the dialysate container 3 to the blood purifier 10. The replacement fluid pump 8 sends the replacement fluid contained in the replacement fluid container 4 to the vein-side blood circuit 13, thereby mixing the replacement fluid into blood purified by the blood purifier 10. The filtrate pump 9 sends filtrate generated by hemofiltration and dialysis (blood purification) of the blood purifier 10, into the filtrate container 5.

The blood purifier 10 has a hemofiltration membrane and a dialysis membrane therein. The blood purifier 10 performs hemofiltration on blood taken from the patient A using the hemofiltration membrane, and also performs dialysis on the blood, using the dialysis membrane and dialysate from the dialysate container 3. In short, the blood purifier 10 purifies blood taken from the patient A. The artery-side blood circuit 11 is a traveling path of blood from the patient A to the blood purifier 10. The dialysate supply channel 12 is a traveling path of dialysate from the dialysate container 3 to the blood purifier 10. The vein-side blood circuit 13 is a traveling path of blood purified by the blood purifier 10 back to the patient A. The filtrate discard channel 14 is a traveling path of filtrate from the blood purifier 10 to the filtrate container 5. Each of the artery-side blood circuit 11, the dialysate supply channel 12, the vein-side blood circuit 13, and the filtrate discard channel 14 is a tube made of a predetermined synthetic resin.

Figure 4:
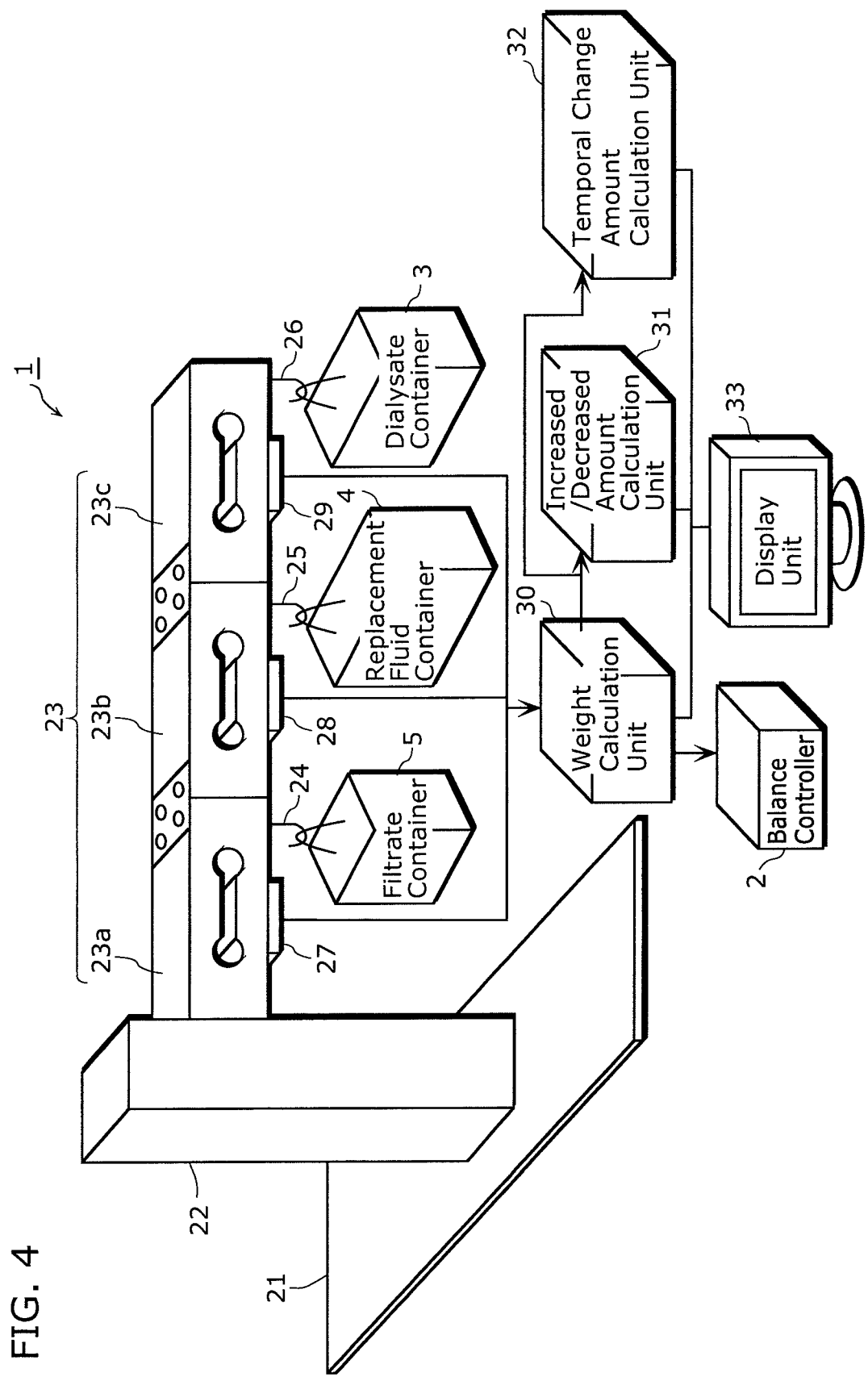
FIG. 4 is a block diagram of a weight sensor 1 according to the first embodiment.

FIG. 4 is a diagram showing a structure of the weight sensor 1 according to the first embodiment. The weight sensor 1 according to the first embodiment is, as described previously, used to balance between (i) a total flow rate of using dialysate and using replacement fluid and (ii) a flow rate of discarding filtrate. The weight sensor 1 detects a weight, a flow rate that is a temporal change amount, and the like regarding each of dialysate, replacement fluid, and filtrate. Then, the weight sensor 1 displays the detection results. As shown in FIG. 4, the weight sensor 1 includes a base 21, a pillar 22, an arm 23, a filtrate holder 24, a replacement fluid holder 25, a dialysate holder 26, a first strain value sensor 27, a second strain value sensor 28, a third strain value sensor 29, a weight calculation unit 30, an increased/decreased amount calculation unit 31, a temporal change amount calculation unit 32, and a display unit 33. The weight sensor 1 also includes, as shown in FIG. 4, a balance controller 2, a dialysate container 3, a replacement fluid container 4, and a filtrate container 5.

The base 21 is, for example, a flat plate made of aluminum. The pillar 22 is, for example, a bar-shaped member made of aluminum, and is fixed on the base 21 in perpendicular to the base 21. The arm 23 is a square bar having one end fixed to the pillar 22 and the other end that is a free end, so that the arm 23 is perpendicular to the pillar 22, in other words, in parallel to the base 21, namely, horizontally. As shown in FIG. 4, the arm 23 is a member comprised of the first square bar 23a, the second square bar 23b, and the third square bar 23c which are connected in series. In more detail, one end of the first square bar 23a is connected in series with one end of the second square bar 23b, and the other end of the second square bar 23b is connected in series with one end of the third square bar 23c. The other end of the first square bar 23a is fixed to the pillar 22. The first square bar 23a, the second square bar 23b, and the third square bar 23c are, for example, square bars made of aluminum. As shown in FIG. 4, each of the first square bar 23a, the second square bar 23b, and the third square bar 23c has a through-hole penetrating horizontally and in perpendicular to a longitudinal direction of the arm 23. A cross section of the through-hole is bone-shaped. More specifically, a shape of the through-hole in a cross section is symmetry with respect to a bisector of a vertical line segment of the cross section of the through-hole, and also symmetry with respect to a bisector of a line segment along the longitudinal direction of the arm 23 in the cross section of the through-hole. Here, a size of each of an end closer to the pillar 22 and the other end closer to the free end in the cross section of the through-hole is larger than a size of a central part of the cross section of the through-hole between the ends.

The filtrate holder 24 is a member for holding the filtrate container 5, and provided on a surface of the first square bar 23a facing the base 21. The filtrate holder 24 is located between the through-hole of the first square bar 23a and the free end of the arm 23. The replacement fluid holder 25 is a member for holding the replacement fluid container 4, and provided on a surface of the second square bar 23b facing the base 21. The replacement fluid holder 25 is located between the through-hole of the second square bar 23b and the free end of the arm 23. The dialysate holder 26 is a member for holding the dialysate container 3, and provided on a surface of the third square bar 23c facing the base 21. The dialysate holder 26 is located between the through-hole of the third square bar 23c and the free end of the arm 23.

The first strain value sensor 27 is a Roberval strain value sensor that is provided on the surface of the first square bar 23a facing the base 21. The first strain value sensor 27 is located between the through-hole of the first square bar 23a and the pillar 22. The first strain value sensor 27 detects an amount of strain (hereinafter, referred to as a "strain value") of the first square bar 23a, which corresponds to a sum (first sum) of: a weight of filtrate in the filtrate container 5 held by the filtrate holder 24; a weight of replacement fluid in the replacement fluid container 4 held by the replacement fluid holder 25; and a weight of dialysate in the dialysate container 3 held by the dialysate holder 26. The second strain value sensor 28 is a Roberval strain value sensor that is provided on the surface of the second square bar 23b facing the base 21. The second strain value sensor 28 is located between the through-hole of the second square bar 23b and the pillar 22. The second strain value sensor 28 detects a strain value of the second square bar 23b, which corresponds to a sum (second sum) of: the weight of the replacement fluid in the replacement fluid container 4 held by the replacement fluid holder 25; and the weight of the dialysate in the dialysate container 3 held by the dialysate holder 26. The third strain value sensor 29 is a Roberval strain value sensor that is provided on the surface of the third square bar 23c facing the base 21. The third strain value sensor 29 is located between the through-hole of the third square bar 23c and the pillar 22. The third strain value sensor 29 detects a strain value of the third square bar 23c, which corresponds to a sum (third sum) that is the weight of the dialysate in the dialysate container 3 held by the dialysate holder 26.

The weight calculation unit 30 calculates a sum (the first sum) of: the weight of the filtrate in the filtrate container 5; the weight of the replacement fluid in the replacement fluid container 4; and the weight of the dialysate in the dialysate container 3, using the result detected by the first strain value sensor 27 and a relationship between the detected strain value and the weights. The weight calculation unit 30 also calculates a sum (the second sum) of: the weight of the replacement fluid in the replacement fluid container 4; and the weight of the dialysate in the dialysate container 3, using the result detected by the second strain value sensor 28 and a relationship between the detected strain value and the weights. The weight calculation unit 30 further calculates a sum (the third sum) that is the weight of the dialysate in the dialysate container 3, using the result detected by the third strain value sensor 29 and a relationship between the detected strain value and the weight. In addition, the weight calculation unit 30 calculates the weight of the filtrate in the filtrate container 5 by subtracting the second sum from the first sum, and the weight of the replacement fluid in the replacement fluid container 4 by subtracting the third sum from the second sum.

The increased/decreased amount calculation unit 31 calculates: an amount of increase in a weight of the filtrate in the filtrate container 5 calculated by the weight calculation unit 30 from an initial weight of the filtrate; an amount of decrease in a weight of the replacement fluid in the replacement fluid container 4 calculated by the weight calculation unit 30 from an initial weight of the replacement fluid; and an amount of decrease in a weight of the dialysate in the dialysate container 3 calculated by the weight calculation unit 30 from an initial weight of the dialysate. In other words, the increased/decreased amount calculation unit 31 calculates: a weight of filtrate which has been discarded; a weight of replacement fluid which has been used; and a weight of dialysate which has been used.

Figure 5A:
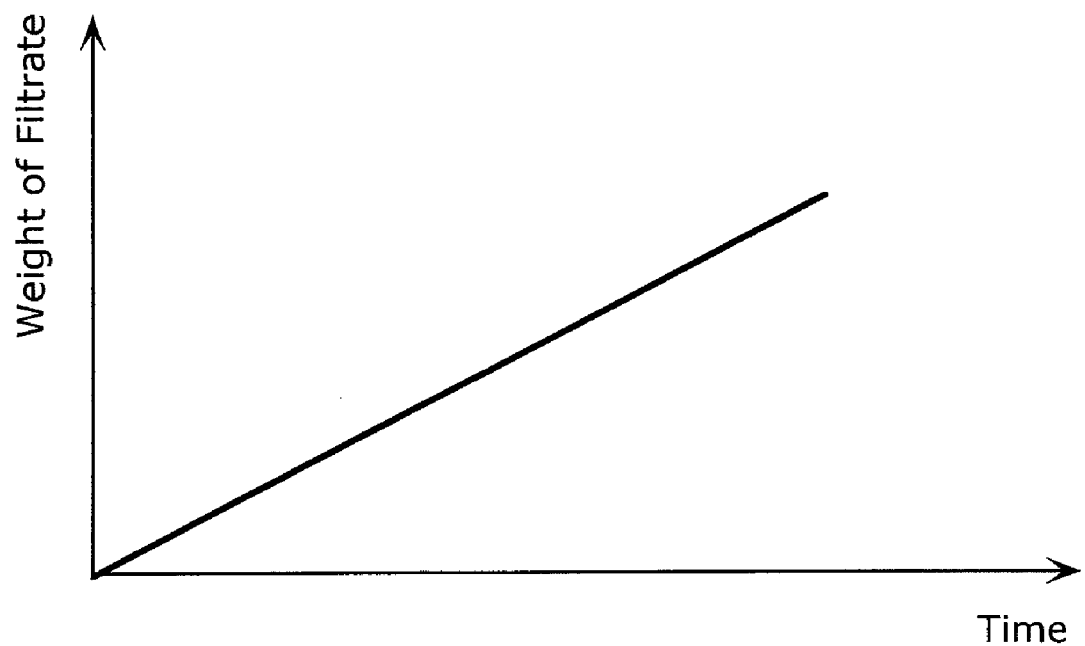
FIG. 5A is a graph plotting increase in a weight of discarded filtrate as time passes.
Figure 5B:
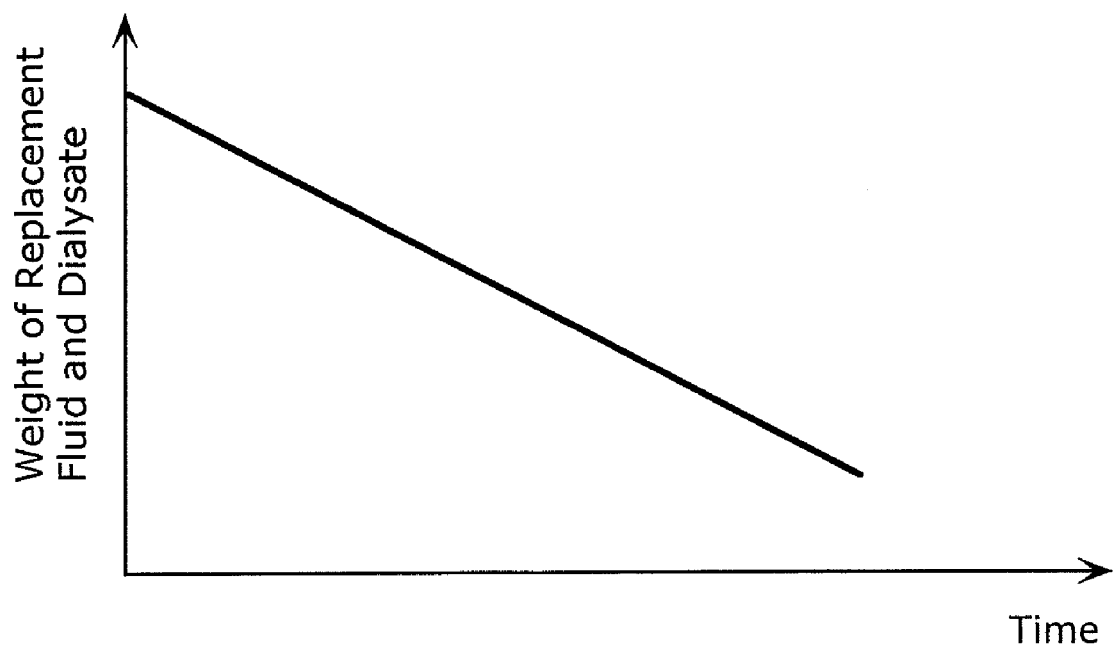
FIG. 5B is a graph plotting decrease in a total weight of used replacement fluid and used dialysate as time passes.

Based on the weight of the filtrate in the filtrate container 5, the weight of the replacement fluid in the replacement fluid container 4, and the weight of the dialysate in the dialysate container 3 which have been calculated by the weight calculation unit 30, the temporal change amount calculation unit 32 calculates: a flow rate of the filtrate contained in the filtrate container 5; a flow rate of the replacement fluid contained in the replacement fluid container 4; and a flow rate of the dialysate contained in the dialysate container 3. Here, FIGS. 5A and 5B show how (A) a weight of discarded filtrate and (B) a total weight of used replacement fluid and used dialysate change as time passes, respectively. FIG. 5A is a graph plotting an increase of a weigh of discarded filtrate as time passes. FIG. 5B is a graph plotting a decrease of a total weight of used replacement fluid and used dialysate as time passes. A weigh of discarded filtrate is increased as time passes as shown in FIG. 5A, and a total weight of used replacement fluid and used dialysate is decreased as time passes as shown in FIG. 5B. Based on the weight of the filtrate in the filtrate container 5, the temporal change amount calculation unit 32 calculates a flow rate of the filtrate contained in the filtrate container 5 which is a temporal amount of increase in a weight of the filtrate in the filtrate container 5. Likewise, based on the weight of the replacement fluid in the replacement fluid container 4, the temporal change amount calculation unit 32 calculates a flow rate of the replacement fluid in the replacement fluid container 4 which is a temporal amount of decrease in a weight of the replacement fluid in the replacement fluid container 4. Also, based on the weight of the dialysate in the dialysate container 3, the temporal change amount calculation unit 32 calculates a flow rate of the dialysate in the dialysate container 3 which is a temporal amount of decrease in a weight of the dialysate in the dialysate container 3.

The display unit 33 displays the results calculated by the weight calculation unit 30, the increased/decreased amount calculation unit 31, and the temporal change amount calculation unit 32. More specifically, the display unit 33 displays: the weigh of the filtrate in the filtrate container 5; the weight of the replacement fluid in the replacement fluid container 4; the weight of the dialysate in the dialysate container 3; the weight of discarded filtrate; the weight of used replacement fluid; the weight of used dialysate; the flow rate of the filtrate in the filtrate container 5; the flow rate of the replacement fluid in the replacement fluid container 4; and the flow rate of the dialysate in the dialysate container 3. FIG. 6 is a diagram showing one example of a screen on which the display 33 displays the calculation results.

Next, processing performed by the blood purification system according to the first embodiment is described with reference to FIG. 7.

Figure 7:
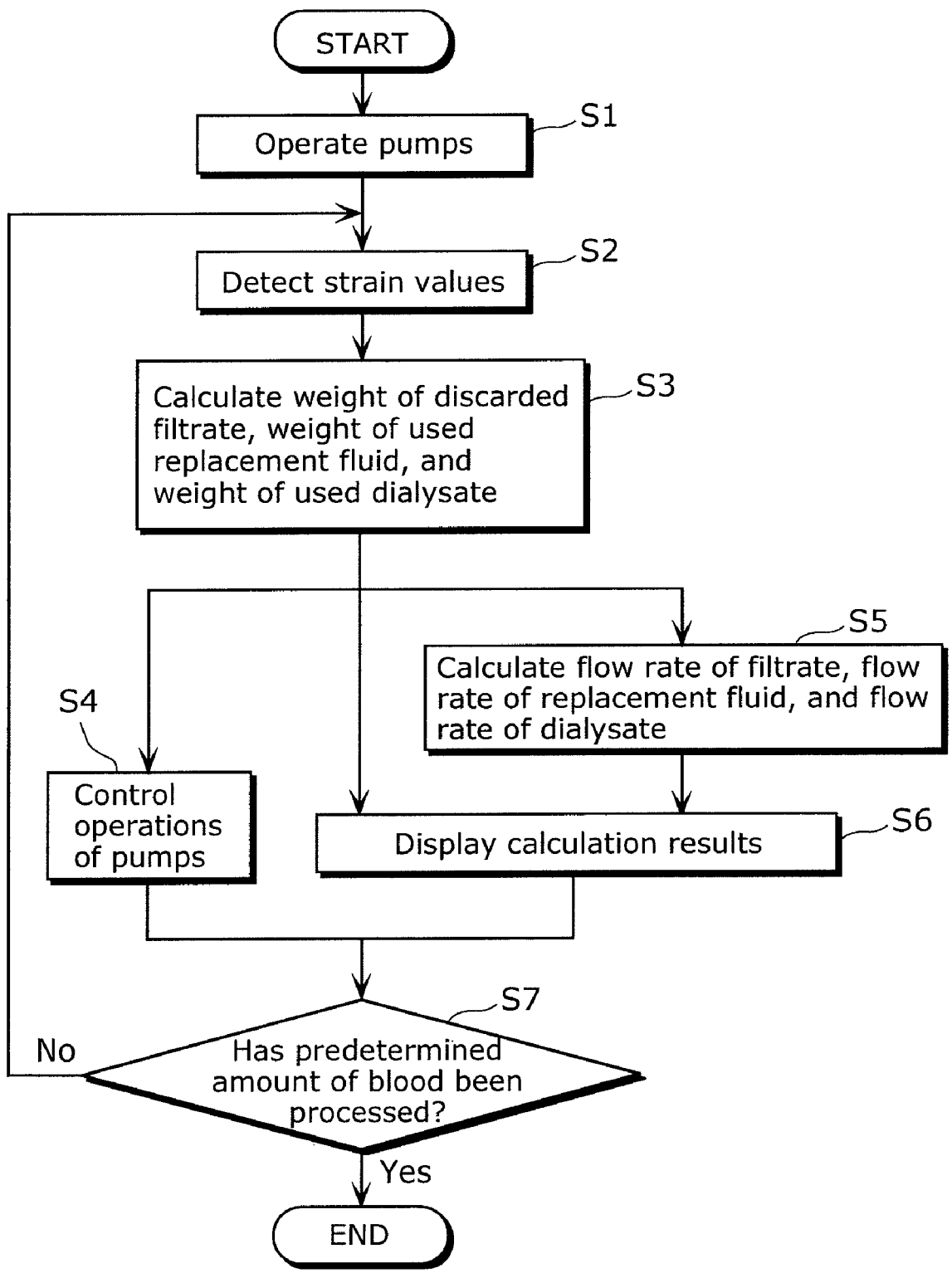
FIG. 7 is a flowchart of processing performed by the blood purification system according to first embodiment.

FIG. 7 is a flowchart of the processing performed by the blood purification system according to first embodiment.

Firstly, in the case of medical treatments using the CHDF to purify blood of the patient A, a physician stores a predetermined amount of replacement fluid into the replacement fluid container 4, and then sets the replacement fluid container 4 to be held by the replacement fluid holder 25 using a handle provided on the top of the replacement fluid container 4. Furthermore, the physician stores a predetermined amount of dialysate into the dialysate container 3, and then sets the dialysate container 3 to be held by the dialysate holder 26 using a handle provided on the top of the dialysate container 3. Still further, the physician sets an empty filtrate container 5 to be held by the filtrate holder 24 using a handle provided on the top of the filtrate container 5. Then, the physician connects the artery-side blood circuit 11 and the vein-side blood circuit 13 with the patient A, and then turns switches of the blood pump 6, the dialysate pump 7, the replacement fluid pump 8, and the filtrate pump 9 to be ON, so that a flow rate of the dialysate, a flow rate of the replacement fluid, and a flow rate of the filtrate become respective predetermined flow rates.

When the switches of the pumps are turned ON, operations of the blood pump 6, the dialysate pump 7, the replacement fluid pump 8, the filtrate pump 9 start (S1). In more detail, the blood pump 6 sends blood taken from the patient A to the blood purifier 10 via the artery-side blood circuit 11, and the dialysate pump 7 sends the dialysate contained in the dialysate container 3 to the blood purifier 10 via the dialysate supply channel 12. The blood purifier 10 performs hemofiltration on the blood taken from the patient A, using the hemofiltration membrane, and also performs dialysis on the blood using the dialysis membrane and the dialysate from the dialysate container 3. The blood purified by the blood purifier 10 is returned to the patient A via the vein-side blood circuit 13. Further, the replacement fluid pump 8 sends the replacement fluid contained in the replacement fluid container 4 to the vein-side blood circuit 13, thereby mixing the replacement fluid into the blood purified by the blood purifier 10. As a result, the blood purified by the blood purifier 10 and the replacement fluid are returned to the patient A. Furthermore, the filtrate pump 9 sends the filtrate generated by the hemofiltration and the dialysis of the blood purifier 10, into the filtrate container 5 via the filtrate discard channel 14.

Then, in the weight sensor 1, the first strain value sensor 27 detects a strain value of the first square bar 23a, the second strain value sensor 28 detects a strain value of the second square bar 23b, and the third strain value sensor 29 detects a strain value of the third square bar 23c (S2). The strain value of the first square bar 23a is a strain value corresponding to a sum (first sum) of: a weight of the filtrate in the filtrate container 5 held by the filtrate holder 24; a weight of the replacement fluid in the replacement fluid container 4 held by the replacement fluid holder 25; and a weight of the dialysate in the dialysate container 3 held by the dialysate holder 26. The strain value of the second square bar 23b is a strain value corresponding to a sum (second sum) of: the weight of the replacement fluid in the replacement fluid container 4 held by the replacement fluid holder 25; and the weight of the dialysate in the dialysate container 3 held by the dialysate holder 26. The strain value of the third square bar 23c is a strain value corresponding to on a sum (third sum) that is the weight of the dialysate in the dialysate container 3 held by the dialysate holder 26.

The weight calculation unit 30 calculates a sum (the first sum) of: the weight of the filtrate in the filtrate container 5; the weight of the replacement fluid in the replacement fluid container 4; and the weight of the dialysate in the dialysate container 3, using the result detected by the first strain value sensor 27 and a relationship between the detected strain value and the weights. The weight calculation unit 30 also calculates a sum (the second sum) of: the weight of the replacement fluid in the replacement fluid container 4; and the weight of the dialysate in the dialysate container 3, using the result detected by the second strain value sensor 28 and a relationship between the detected strain value and the weights. The weight calculation unit 30 further calculates a sum (the third sum) that is the weight of the dialysate in the dialysate container 3, using the results detected by the third strain value sensor 29 and a relationship between the detected strain value and the weight. In addition, the weight calculation unit 30 calculates the weight of the filtrate in the filtrate container 5 by subtracting the second sum from the first sum, and the weight of the replacement fluid in the replacement fluid container 4 by subtracting the third sum from the second sum (S3).

Here, if there is a balance between (i) a total flow rate of used dialysate and used replacement fluid and (ii) a flow rate of discarded filtrate, an amount of decrease in dialysate in the dialysate container 3 and replacement fluid in the replacement fluid container 4 becomes equal to an amount of increase in filtrate in the filtrate container 5. This means that, in the above situation, the first sum is not changed as time passes.

Then, the balance controller 2 controls the dialysate pump 7, the replacement fluid pump 8, and the filtrate pump 9 to keep, within respective predetermined ranges, the total flow rate of the using dialysate and using replacement fluid and the flow rate of the discarding filtrate, and at the same time, to keep the first sum to be constant (S4). In more detail, in the balance controller 2, the obtainment unit 41 obtains, from the weight calculation unit 30 of the weight sensor 1, that sum (first sum) of: the weight of the filtrate in the filtrate container 5; the weight of the replacement fluid in the replacement fluid container 4; and the weight of the dialysate in the dialysate container 3. The control unit 42 controls the dialysate pump 7, the replacement fluid pump 8, and the filtrate pump 9 to keep, within respective predetermined ranges, a total flow rate of the using dialysate and using replacement fluid and a flow rate of the discarding filtrate, and at the same time, to keep the first sum to be constant. This achieves a balance between (i) the total flow rate of the using dialysate and the using replacement fluid and (ii) the flow rate of the discarding filtrate.

Based on the results calculated by the weight calculation unit 30, the increased/decreased amount calculation unit 31 calculates: an amount of increase in a weight of the filtrate in the filtrate container 5 from an initial weight of the filtrate; an amount of decrease in a weight of the replacement fluid in the replacement fluid container 4 from an initial weight of the replacement fluid; and an amount of decrease in a weight of the dialysate in the dialysate container 3 from an initial weight of the dialysate. In other words, the increased/decreased amount calculation unit 31 calculates: a weight of filtrate which has been discarded; a weight of replacement fluid which has been used; and a weight of dialysate which has been used.

Based on the results calculated by the weight calculation unit 30, the temporal change amount calculation unit 32 calculates: a temporal change amount in a weight of the dialysate container 3; a temporal change amount in a weight of the replacement fluid container 4; and a temporal change amount in a weight of the filtrate container 5. In other words, the temporal change amount calculation unit 32 calculates: a flow rate of the filtrate contained in the filtrate container 5; a flow rate of the replacement fluid contained in the replacement fluid container 4; and a flow rate of dialysate contained in the dialysate container 3 (S5). In more detail, the temporal change amount calculation unit 32 calculates the flow rate of the filtrate, by dividing the temporal change amount of the weight of the filtrate calculated by the weight calculation unit 30, by a specific gravity of the filtrate. The temporal change amount calculation unit 32 also calculates the flow rate of the replacement fluid, by dividing the temporal change amount of the weight of the replacement fluid calculated by the weight calculation unit 30, by a specific gravity of the replacement fluid. The temporal change amount calculation unit 32 further calculates the flow rate of the dialysate, by dividing the temporal change amount of the weight of the dialysate calculated by the weight calculation unit 30, by a specific gravity of the dialysate.

The display unit 33 displays, as shown in FIG. 6, the results calculated by the weight calculation unit 30, the increased/decreased amount calculation unit 31, and the temporal change amount calculation unit 32 (S6). More specifically, the display unit 33 displays: the weigh of the filtrate in the filtrate container 5; the weight of the replacement fluid in the replacement fluid container 4; the weight of the dialysate in the dialysate container 3; the weight of the discarded filtrate; the weight of the used replacement fluid; the weight of the used dialysate; the flow rate of the filtrate contained in the filtrate container 5; the flow rate of the replacement fluid contained in the replacement fluid container 4; and the flow rate of the dialysate contained in the dialysate container 3.

The balance controller 2 determines whether or not a predetermined amount of blood has been purified (S7). If it is determined that the predetermined amount of blood has not yet been purified (No at S7), the processing returns to Step S2 where the first strain value sensor 27, the second strain value sensor 28, and the third strain value sensor 29 detect strain values of respective predetermined parts. On the other hand, if it is determined that the predetermined amount of blood has been purified (Yes at S7), the processing performed by the blood purification system according to the first embodiment completes.

As described above, in the blood purification system according to the first embodiment, the balance controller 2 controls operations of the dialysate pump 7, the replacement fluid pump 8, and the filtrate pump 9, in order not to change a sum (first sum) of: a weight of filtrate in the filtrate container 5; a weight of replacement fluid in the replacement fluid container 4; and a weight of dialysate in the dialysate container 3. This achieves a balance between (i) a total flow rate of using dialysate and using replacement fluid and (ii) a flow rate of discarding filtrate.

In addition, in the blood purification system according to the first embodiment, the display unit 33 displays the results calculated by the weight calculation unit 30, the increased/decreased amount calculation unit 31, and the temporal change amount calculation unit 32. In other words, the blood purification system according to the first embodiment displays: a weight of discarded filtrate; a weight of used replacement fluid; a weight of used dialysate; a flow rate of discarding filtrate; a flow rate of using replacement fluid; and a flow rate of using dialysate. Thereby, a physician can learn: the weight of discarded filtrate; the weight of used replacement fluid; the weight of used dialysate; the flow rate of discarding filtrate; the flow rate of using replacement fluid; and the flow rate of using dialysate.

This means that the balance controller 2 according to the first embodiment can achieve a balance between (i) a flow rate of blood taken from a patient and (ii) a total flow rate of blood returned to the patient and replacement fluid supplied to the patient, using the calculation results obtained by the weight sensor 1. In addition, the weight sensor 1 according to the first embodiment correctly calculates: a weight of discarded filtrate; a weight of used replacement fluid; a weight of used dialysate; a flow rate of discarding filtrate; a flow rate of using replacement fluid; a flow rate of using dialysate, and then displays the calculation results.

It should be noted that a set of the filtrate holder 24, the replacement fluid holder 25, and the dialysate holder 26 in the first embodiment is an example of the "n holders" in the weight sensor according to the aspect of the present invention. It should also be noted that a set of the first strain value sensor 27, the second strain value sensor 28, the third strain value sensor 29 in the first embodiment is an example of the "n strain value sensors" in the weight sensor according to the aspect of the present invention.

It should also be note that the arm 23 is not limited to have a structure comprising of the first square bar 23*a*, the second square bar 23*b*, and the third square bar 23*c*. That is, the structure of the arm is not limited to have a plurality of square bars. The arm may be comprised of a single square bar only. When the arm is comprised of a single square bar, the arm has a through-hole between the pillar 22 and a holder proximate to the pillar 22, and other through-holes each provided between two neighboring holders. These through-holes are penetrating horizontally and in a direction perpendicular to the arm having a linear shape.

It should also be note that, when the arm 23 is comprised of a plurality of bar-shaped members, each of the bar-shaped members is not limited to be a square bar, but may be a round bar or the like. When the arm 23 is comprised of a single bar-shaped member, the bar-shaped member is not limited to be a square bar, but may be a round bar or the like.

Figure 8:
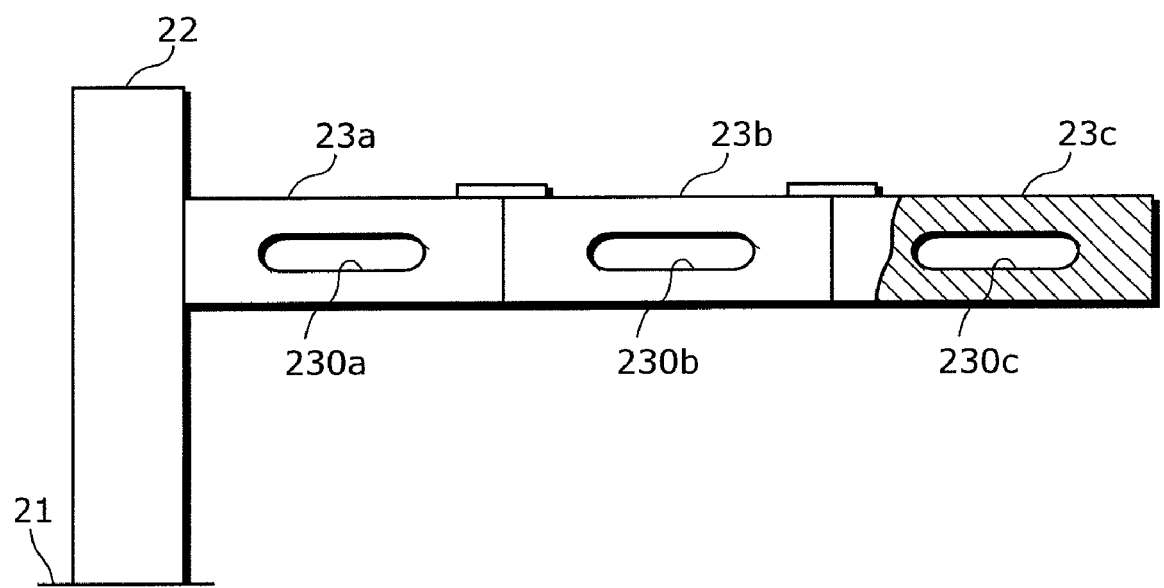
FIG. 8 is a diagram showing a part of a structure of a weight sensor 1 according to a first modification of the first embodiment.

It should also be note that the shape of the though-hole provided in the arm 23 in the cross section is not limited to the bone shape, but the shape may be an ellipse or the like as shown as a through-hole 230*a*, a through-hole 230*b*, and a through-hole 230*c* in FIG. 8. Here, it is preferable that the shape of the through-hole in the cross section is symmetry with respect to a bisector of a line segment perpendicular to a longitudinal direction of the arm 23 in the cross section, and also symmetry with respect to a bisector of a line segment along the longitudinal direction of the arm 23 in the cross section.

Figure 9:
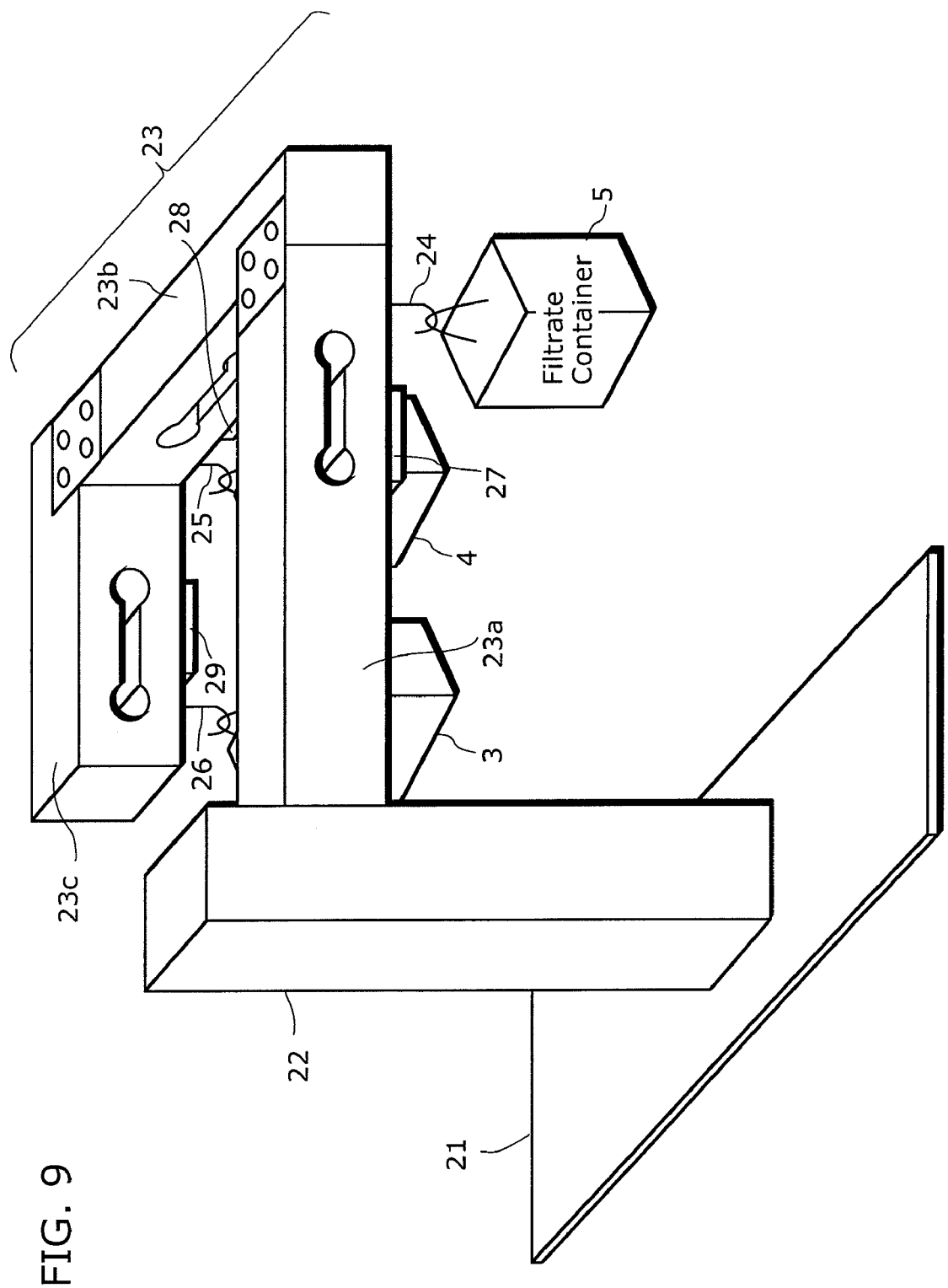
FIG. 9 is a diagram showing a part of a structure of a weight sensor 1 according to a second modification of the first embodiment.

It should also be note that, when the arm 23 is comprised of a plurality of bar-shaped members, the plurality of bar-shaped members in the arm 23 may be connected in a broken line so that the members form a square without one side as viewed from above, as shown in FIG. 9, for example. The arm 23 may also be a single member having a shape of a broken line. The arm 23 may also have a shape of a circular or a curb so that the arm forms a "U" shape as viewed from above.

It should also be note that the arm 23 may be made of any material such as titanium, if the material results in accurate detection of strain values.

It should also be noted that the first strain value sensor 27, the second strain value sensor 28, and the third strain value sensor 29 are not limited to the Roberval strain value sensors.

Each of the first strain value sensor 27, the second strain value sensor 28, and the third strain value sensor 29 may be anything capable of detecting a strain value that is a change in strain of the corresponding square bar resulting from a weight of the corresponding square bar. It should also be note that the arm 23 may be without any through-holes. In other words, the arm 23 may be comprised of one or more bar-shaped member without any through-hole, as far as the arm 23 has a means for detecting strain values with a high accuracy.

Second Embodiment

The following describes a blood purification system according to a second embodiment of the present invention.

It has been described in the first embodiment that the blood purification system is used for medical treatments using the CHDF to purify blood of the patient A. However, the blood purification system according to the present invention sometimes uses the CHF in blood purification.

In the second embodiment of the present invention, a blood purification system using the CHF to purify blood is described.

In the CHF, as previously explained, blood taken from a patient is supplied to a blood purifier having a hemofiltration membrane and applied with hemofiltration using the hemofiltration membrane, then the purified blood is returned to the patient, and waste products and solvent in the blood resulting from the hemofiltration is discarded. In addition, replacement fluid is supplied to blood of the patient. The above processing is performed continuously and slowly. Therefore, the medical treatments using the CHF differs from the medical treatments using the CHDF in that dialysate is not used. However, a balance between (i) a flow rate of using replacement fluid and (ii) a flow rate of discarding filtrate should be achieved to prevent deterioration of the patient's condition.

Figure 10:
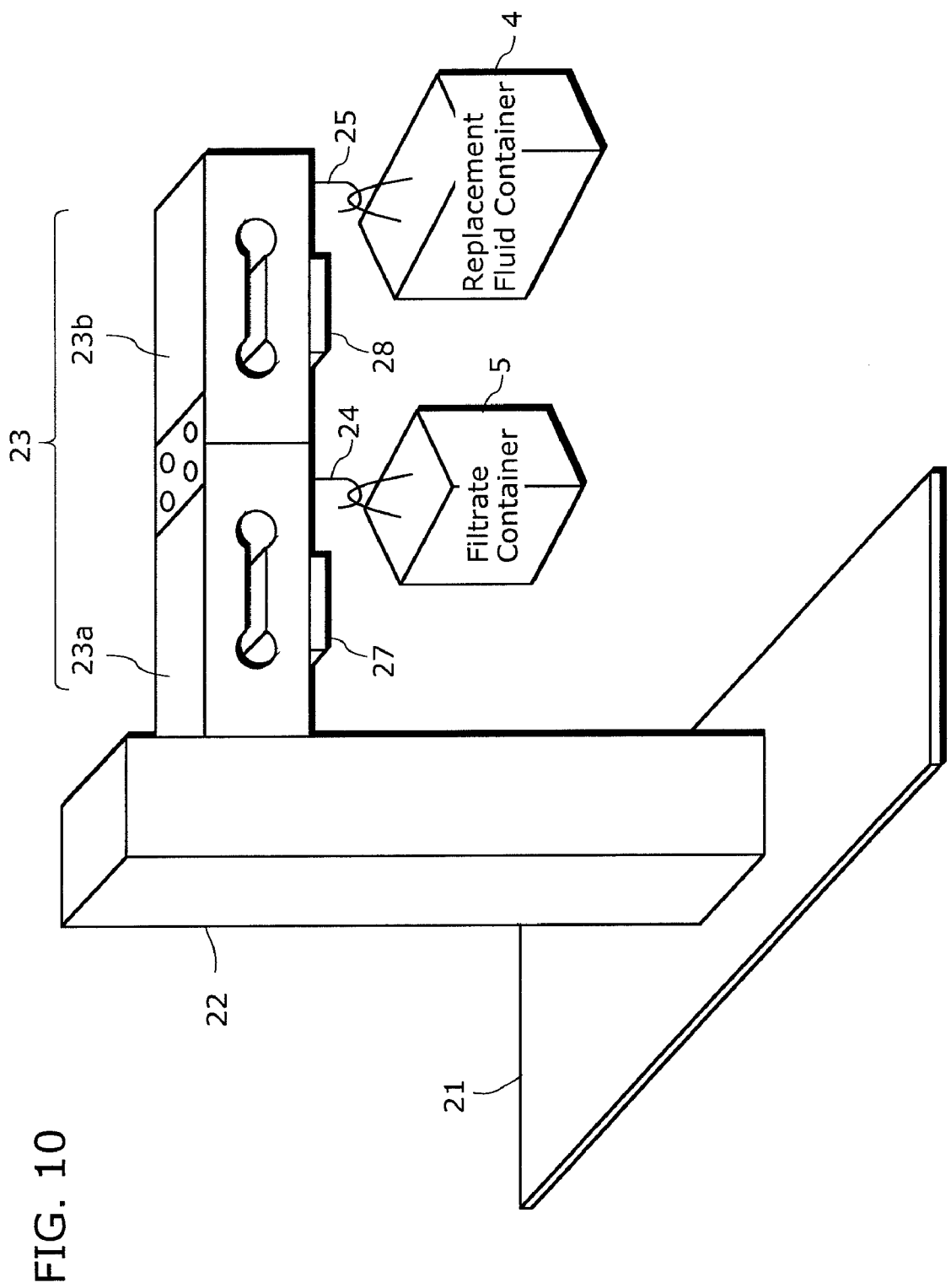
FIG. 10 is a diagram showing a part of a structure of a weight sensor 1 according to the second embodiment of the present invention.

Therefore, the blood purification system of the second embodiment differs from the blood purification system of the first embodiment of FIGS. 3 and 4 in that the arm 23 in the weight sensor 1 is replaced by a structure as shown in FIG. 10. FIG. 10 is a diagram showing a part of the weight sensor 1 according to the second embodiment. The weight sensor 1 of the second embodiment has most of the same elements as the elements of the weight sensor 1 of the first embodiment. Therefore, FIG. 10 shows only some of the elements in the weight sensor 1 of the second embodiment in order to clearly show a difference from the weight sensor 1 of the first embodiment. In more detail, FIG. 10 shows the base 21, the pillar 22, an arm 23, the filtrate holder 24, the replacement fluid holder 25, a first strain value sensor 27, a second strain value sensor 28 in the weight sensor 1 according to the second embodiment. FIG. 10 also shows the replacement fluid container 4 and the filtrate container 5.

In the blood purification system according to the second embodiment, the first strain value sensor 27 detects a strain value of the first square bar 23a corresponding to a sum (fourth sum) of: a weight of filtrate in the filtrate container 5 held by the filtrate holder 24; and a weight of replacement fluid in the replacement fluid container 4 held by the replacement fluid holder 25. The second strain value sensor 28 detects a strain value of the second square bar 23b corresponding to the weight (fifth sum) of the replacement fluid in the replacement fluid container 4 held by the replacement fluid holder 25.

The weight calculation unit 30 calculates a sum of: the weigh of the filtrate in the filtrate container 5; and the weight of the replacement fluid in the replacement fluid container 4, using the results detected by the first strain value sensor 27 and a relationship between the detected strain value and the weights. The weight calculation unit 30 also calculates the weight of the replacement fluid in the replacement fluid container 4, using the result detected by the second strain value sensor 28 and a relationship between the detected strain value and the weight. The weight calculation unit 30 further calculates the weight of the filtrate in the filtrate container 5, by subtracting the fifth sum from the fourth sum.

In the meanwhile, when there is a balance between (i) a flow rate of using replacement fluid and (ii) a flow rate of discarding filtrate, an amount of decrease in replacement fluid contained in the replacement fluid container is equal to an amount of increase in filtrate contained in the filtrate container 5, per unit time. This means that the fourth sum is not changed even if time passes.

Then, the balance controller 2 controls operations of the replacement fluid pump 8 and the filtrate pump 9 in order to keep, within respective predetermined flow rates, a flow rate of using replacement fluid and a flow rate of discarding filtrate, and to thereby keep the fourth sum to be constant. In more detail, in the balance controller 2, the obtainment unit 41 obtains, from the weight calculation unit 30 in the weight sensor 1, a sum (the fourth sum) of: the weight of the filtrate in the filtrate container 5; and the weight of the replacement fluid in the replacement fluid container 4. The control unit 42 controls operations of the replacement fluid pump 8 and the filtrate pump 9 in order to keep, within respective predetermined flow rates, a flow rate of using replacement fluid and a flow rate of discarding filtrate, and to thereby keep the fourth sum to be constant. As a result, a balance between (i) a flow rate of using replacement fluid and (ii) a flow rate of discarding filtrate is achieved.

The increased/decreased amount calculation unit 31 calculates: an amount of increase in a weight of filtrate in the filtrate container 5 calculated by the weight calculation unit 30 from an initial weight of filtrate; and an amount of decrease in a weight of replacement fluid in the replacement fluid container 4 calculated by the weight calculation unit 30 from an initial weight of replacement fluid. In short, the increased/decreased amount calculation unit 31 calculates a weight of filtrate which has been discarded and a weight of replacement fluid which has been used.

Based on the weight of the filtrate in the filtrate container and the weight of the replacement fluid in the replacement fluid container 4 calculated by the weight calculation unit 30, the temporal change amount calculation unit 32 calculates: a flow rate of filtrate contained in the filtrate container 5; and a flow rate of replacement fluid contained in the replacement fluid container 4.

Based on the weight of the filtrate in the filtrate container 5, the temporal change amount calculation unit 32 calculates a flow rate of the filtrate contained in the filtrate container 5, which is an amount of temporal increase in a weight of the filtrate in the filtrate container 5. Likewise, based on the weight of the replacement fluid in the replacement fluid container 4, the temporal change amount calculation unit 32 calculates a flow rate of the replacement fluid contained in the replacement fluid container 4, which is an amount of temporal decrease in a weight of the replacement fluid in the replacement fluid container 4.

The display unit 33 displays the results calculated by the weight calculation unit 30, the increased/decreased amount calculation unit 31, and the temporal change amount calculation unit 32. In other words, the display unit 33 displays: the weigh of the filtrate in the filtrate container 5; the weight of the replacement fluid in the replacement fluid container 4; the weight of discarded filtrate; the weight of used replacement fluid; the flow of the filtrate contained in the filtrate container 5; and the flow rate of the replacement fluid contained in the replacement fluid container 4. Thereby, a physician can learn: the weight of the discarded filtrate; the weight of the used replacement fluid; the flow rate of discarding filtrate, and the flow rate of using replacement fluid.

As described above, the blood purification system according to second embodiment, the balance controller 2 controls operations of the replacement fluid pump 8 and the filtrate pump 9 so that the fourth sum is not changed as time passes. As a result, a balance between (i) a flow rate of using replacement fluid and (ii) a flow rate of discarding filtrate is achieved.

In addition, in the blood purification system according to the second embodiment, the display unit 33 displays the results calculated by the weight calculation unit 30, the increased/decreased amount calculation unit 31, and the temporal change amount calculation unit 32. In more detail, the blood purification system according to the second embodiment displays: the weight of the discarded filtrate; the weight of the used replacement fluid; the flow rate of discarding filtrate; and the flow rate of the using replacement fluid. Thereby, a physician can learn: the weight of discarded filtrate; the weight of used replacement fluid; the flow rate of discarding filtrate; and the flow rate of using replacement fluid.

It has been described in the above embodiments that the weight sensor and the balance controller according to the present invention are used in the blood purification system for performing medical treatments using the CHDF and the CHF to purify blood of the patient A. However, the weight sensor and the balance controller according to the present invention are not limited to be used in the blood purification system for performing medical treatments using the CHDF and the CHF to purify blood of the patient A. The weight sensor according to the present invention can be used to achieve a balance among weights of a plurality of substances and to detect respective weights of the substances. Therefore, although the n holders in the weight sensor according to the aspect of the present invention have been described in the above embodiments as the filtrate holder 24, the replacement fluid holder 25, and the dialysate holder 26, "n" is not limited to 3 or 2. Likewise, the number of the n strain value sensors in the weight sensor according to the aspect of the present invention is not limited. Furthermore, the balance controller according to the present invention achieves a balance among weights of a plurality of substances, using results generated by the weight sensor according to the present invention.

INDUSTRIAL APPLICABILITY

The weight sensor according to the present invention is useful as a device or the like to be used for balancing between (i) a flow rate of blood taken from a patient and (ii) a total flow rate of blood returned to the patient and replacement fluid supplied to the patient, in medical treatments using the CHF or the CHDF to purify blood of a patient such as a patient with renal function insufficiency. Furthermore, the balance controller according to the present invention is useful as a device or the like which achieves the balance between (i) the flow rate of blood taken from the patient and (ii) the total flow rate of the blood returned to the patient and the replacement fluid supplied to the patient, based on results calculated by the weight sensor according to the present invention.

The invention claimed is:

1. A weight sensor comprising:
   a pillar;
   an arm having an end fixed to said pillar and a free end;
   n holders, provided at n locations on a side surface of said arm arranged along a longitudinal direction, respectively, each of which is configured to hold a substance, n being a natural number equal to or greater than two;
   n strain value sensors, provided on said arm in association with n sums, respectively, each of which is configured to detect a strain value of said arm corresponding to a corresponding sum among the n sums, the corresponding sum being a sum of weights of the substances held by said holders ranging from a holder proximate to the free end to a m-th holder counted from said pillar, and m being a natural number ranging from 1 to n; and
   a weight calculation unit configured to calculate the n sums based on results of the detection of said n strain value sensors.

2. The weight sensor according to claim 1,
   wherein said weight calculation unit is configured to calculate the weights of the substances held by said n holders, respectively, based on results of the detection of said n strain value sensors.

3. The weight sensor according to claim 1 further comprising
   a display unit configured to display results of the calculation of said weight calculation unit.

4. The weight sensor according to claim 1,
   wherein said arm is a member including n bar-shaped members connected in series at each end,
   each of said n bar-shaped members has a hole penetrating in a direction perpendicular to the longitudinal direction of said arm without penetrating the side surface, and
   said n holders are provided on said n bar-shaped members, respectively.

5. The weight sensor according to claim 4,
   wherein a shape of the hole in a cross section is symmetry with respect to a bisector of a line segment perpendicular to the longitudinal direction of said arm in the cross section of the hole, and also symmetry with respect to a bisector of a line segment along the longitudinal direction of said arm in the cross section of the hole.

6. The weight sensor according to claim 5,
   wherein a size of each of a closer end and a farther end of the cross section of the hole is larger than a size of a part of the cross section of the hole between the closer end and the farther end, the closer end being closer to said pillar and an farther end being farther from said pillar.

7. The weight sensor according to claim 4,
   wherein said n strain value sensors are Roberval strain value sensors provided on said n bar-shaped members, respectively.

8. The weight sensor according to claim 1,
   wherein said arm has holes each of which penetrates in a direction perpendicular to the longitudinal direction of said arm without penetrating the side surface, the holes being provided between said pillar and the holder proximate to said pillar and between two neighboring holders, respectively.

9. The weight sensor according to claim 8,
   wherein a shape of each of the holes in a cross section is symmetry with respect to a bisector of a line segment perpendicular to the longitudinal direction of said arm in the cross section of the hole, and also symmetry with respect to a bisector of a line segment along the longitudinal direction of said arm in the cross section of the hole.

10. The weight sensor according to claim 9,
wherein a size of each of a closer end and a farther end of the cross section of the hole is larger than a size of a part of the cross section of the hole between the closer end and the farther end, the closer end being closer to said pillar and an farther end being farther from said pillar.

11. The weight sensor according to claim 8,
wherein said n strain value sensors are Roberval strain value sensors, and
said n strain value sensors are provided between said pillar and the holder proximate to said pillar and between the two neighbor holders, respectively and separately.

12. The weight sensor according to claim 1 further comprising,
an increased/decreased amount calculation unit configured to calculate an amount of increase or decrease in a weight of the substance held by each of said n holders from an initial weight of the substance, based on results of the calculation of said n weight calculation units.

13. The weight sensor according to claim 1 further comprising
a temporal change amount calculation unit configured to calculate an amount of a temporal change in a weight of the substance held by each of said n holders, based on results of the calculation of said n weight calculation units.

14. A balance controller comprising:
an obtainment unit configured to obtain a sum of weights of substances calculated by the weight sensor according to claim 1, the substances being held by the holders that are from a holder proximate to the free end of the arm to a holder proximate to said pillar; and
a control unit configured to control temporal change amounts of the weights of the substances held by the holders, respectively, in order to keep the sum obtained by said obtainment unit within a predetermined range.

15. The balance controller according to claim 14,
wherein the number of the holders is three,
a first holder in the holders holds filtrate, a second holder in the holders holds replacement fluid, and a third holder in the holders holds dialysate, and
said control unit is configured to keep a sum of a weight of the filtrate, a weight of the replacement fluid, and a weight of the dialysate within a predetermined range, so as to balance between an amount of temporal increase in the filtrate and an amount of temporal decrease in the replacement fluid and the dialysate.

16. The balance controller according to claim 14,
wherein the number of the n holders is two,
a first holder in the holders holds filtrate, and a second holder in the holders holds replacement fluid, and
said control unit is configured to keep a sum of a weigh of the filtrate and a weight of the replacement fluid within a predetermined range, so as to balance between an amount of temporal increase in the filtrate and an amount of temporal decrease in the replacement fluid.

* * * * *